US00PP31005P3

(12) United States Plant Patent
Warner

(10) Patent No.: US PP31,005 P3
(45) Date of Patent: Nov. 5, 2019

(54) FLORIBUNDA ROSE PLANT NAMED 'CHEWGEWEST'

(50) Latin Name: ***Rosa* hybrid**
Varietal Denomination: CHEWGEWEST

(71) Applicant: Christopher Hugh Warner, Brockton (GB)

(72) Inventor: Christopher Hugh Warner, Brockton (GB)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,310

(22) Filed: Sep. 2, 2016

(65) Prior Publication Data

US 2018/0070489 P1 Mar. 8, 2018

(51) Int. Cl.
*A01H 5/02* (2018.01)
*A01H 6/74* (2018.01)

(52) U.S. Cl.
USPC ..... Plt./147
CPC ..... *A01H 5/02* (2013.01); *A01H 5/0222* (2013.01); *A01H 6/749* (2018.05)

(58) Field of Classification Search
USPC ..... Plt./101, 102, 106, 109, 113, 116, 120, Plt./123, 127, 130, 136, 141, 147
See application file for complete search history.

(56) References Cited

PUBLICATIONS

World Federation of Rose Societies website. http://www.worldrose.org/trials/2015/hague/hague16.asp. retrieved Oct. 15, 2017. 1 page.*

* cited by examiner

*Primary Examiner* — Susan Beth McCormick Ewoldt
*Assistant Examiner* — Karen M Redden
(74) *Attorney, Agent, or Firm* — Cassandra Bright

(57) ABSTRACT

A new and distinct *Rosa* cultivar, for garden use named 'CHEWGEWEST' is disclosed, characterized by a distinctive deep peach flowers, with petals in an even, double whorl. Plants have an above average resistance to diseases and repeat bloom rapidly. The new variety is a *Rosa*, normally produced as an outdoor garden or container plant.

3 Drawing Sheets

Latin name of the genus and species: *Rosa* hybrid.
Variety denomination: 'CHEWGEWEST'.

BACKGROUND OF THE INVENTION

The new *Rosa* cultivar is a product of a planned breeding program conducted by Christopher Hugh Warner in Brockton, Newport Shromshire, United Kingdom. The objective of the propagation was to produce new *Rosa* varieties for ornamental commercial applications. The cross resulting in this new variety was made during June of 2006.

The seed parent is the unpatented variety referred to as *Rosa* hybrid 'Gelber Engel'. The pollen parent is the unpatented variety referred to as *Rosa* hybrid 'Westheitz'. The new variety was discovered in June of 2007 by the inventor in a group of seedlings resulting from the 2006 crossing, in a research greenhouse in Brockton, Newport Shromshire, United Kingdom.

Asexual reproduction of the new cultivar was performed by softwood cuttings at a commercial nursery in Brockton, UK during July 2008. Subsequent propagation has shown that the unique features of this cultivar are stable and reproduced true to type in successive generations.

SUMMARY OF THE INVENTION

The cultivar 'CHEWGEWEST' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CHEWGEWEST' These characteristics in combination distinguish 'CHEWGEWEST' as a new and distinct *Rosa* cultivar:

1. Peach colored flowers.
2. Strong disease resistance.
3. Compact plant habit.
4. Dense lateral branching.

Plants of the new cultivar 'CHEWGEWEST' are similar to plants of the seed parent in most horticultural characteristics, however, plants of the new cultivar 'CHEWGEWEST' differ in the following:

1. Flower color of the new variety is peach, flower color of the seed parent is pale yellow.
2. Plant habit of the new variety is even and controlled, plant habit of the seed parent is somewhat irregular.

Plants of the new cultivar 'CHEWGEWEST' are similar to plants of the pollen parent in most horticultural characteristics, however, plants of the new cultivar 'CHEWGEWEST' differ in the following:

1. Flower color of the new variety is peach, flower color of the pollen parent is orange.
2. Petal arrangement of the new variety is evenly whorled, petal arrangement of the pollen parent is loosely and irregularly whorled.

COMMERCIAL COMPARISON

Plants of the new cultivar 'CHEWGEWEST' can be compared to the commercial variety *Rosa* 'ChewniceBell', U.S. Plant Pat. No. 26,532. These varieties are similar in most horticultural characteristics; however 'CHEWGEWEST' differs in the following:

1. Flower color is peach. Comparator flower is yellow and pink.
2. The new variety has more petals per flower.

Plants of the new cultivar 'CHEWGEWEST' can also be compared to the commercial variety *Rosa* 'Chewpatout', U.S. Plant Pat. No. 28,395. These varieties are similar in most horticultural characteristics, including disease resistance and flower shape. However 'CHEWGEWEST' differs in the following:

1. Flower color is peach. Comparator flower is red.

BRIEF DESCRIPTION OF THE PHOTOGRAPHS

The accompanying photograph in FIG. 1 illustrates in full color a typical 2 year old plant of the new variety, in a 2 gallon pot.

Figure 1:
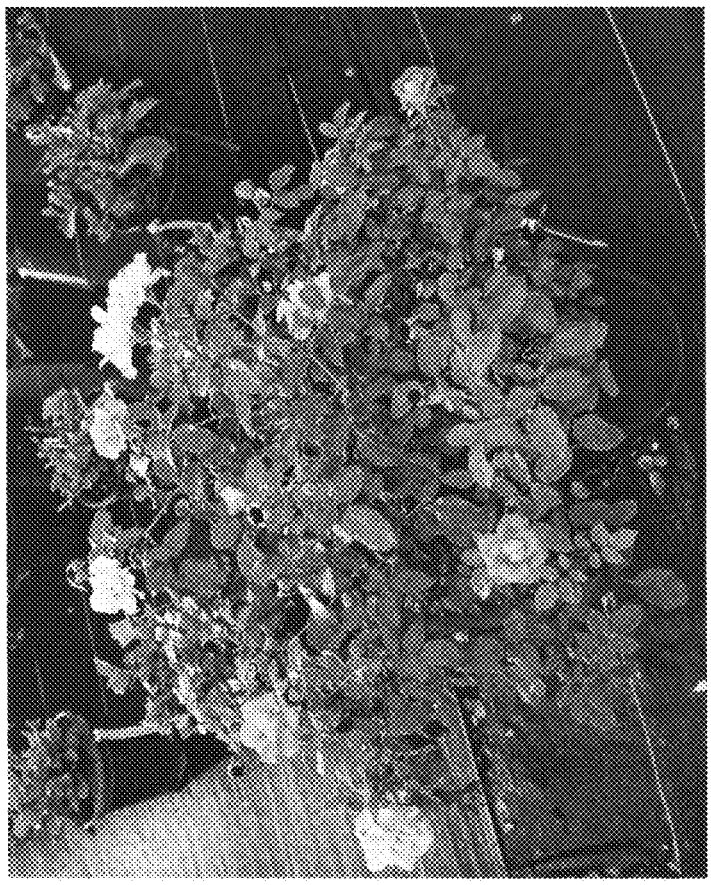
Figure 2:
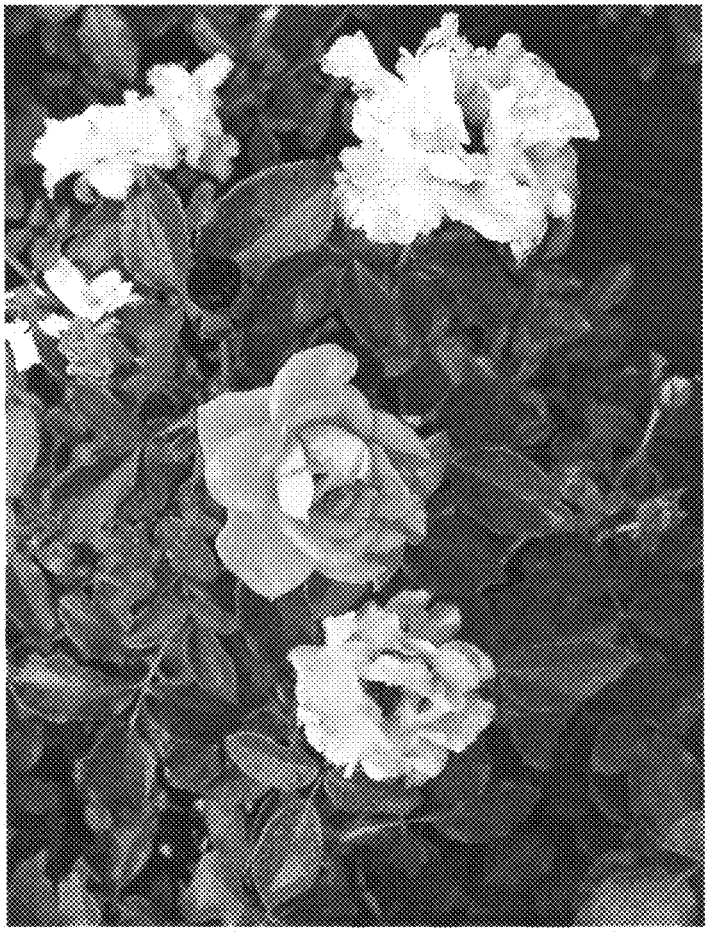
FIG. 2 illustrates typical flowers of 'CHEWGEWEST', including the range of colors aging flowers exhibit.
Figure 3:
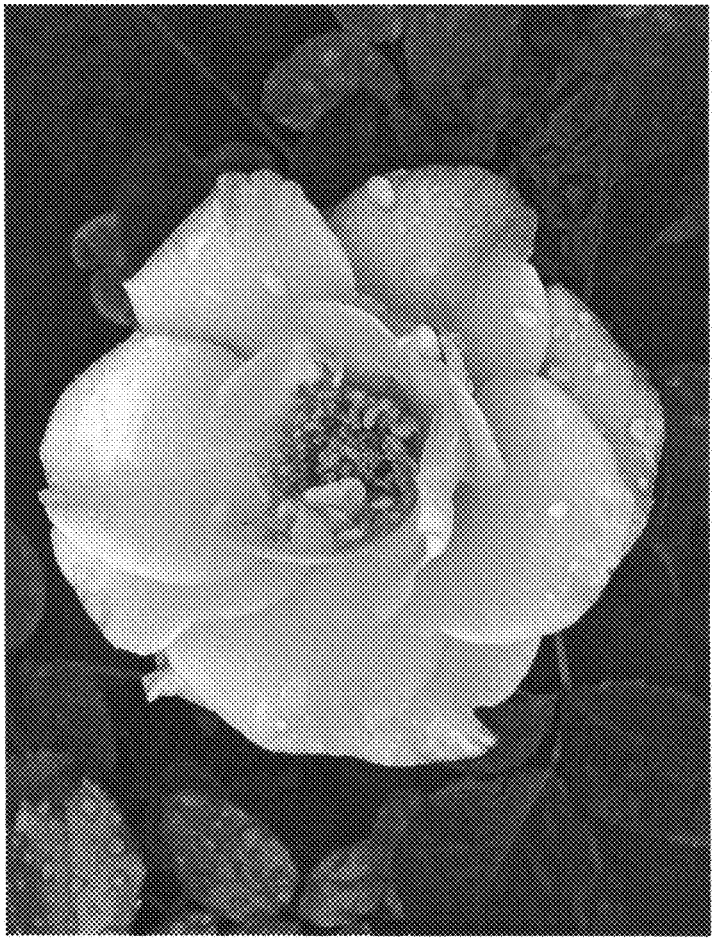
FIG. 3 illustrates a close up of a single mature flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'CHEWGEWEST' plants grown in a poly house greenhouse, in Grand Haven, Mich. The growing temperature ranged from approximately 18° C. to 27° C. during the day and from approximately 5° C. to 10° C. during the night. General light conditions are bright, normal sunlight. Measurements and numerical values represent averages of typical plant types.

Botanical classification: *Rosa* 'CHEWGEWEST'.

Commercial classification: Landscape floribunda.

Propagation:

*Time to initiate roots.*—About 30 days at approximately 20° C.

*Time to produce a rooted young plant.*—About 120 days at approximately 20° C.

*Root description.*—Moderately free branching, medium thickness, both fibrous and fleshy roots present. Roots a creamy white color, not accurately measured with R.H.S. chart.

Plant:

*Age of plant described.*—Approximately 2 to 3 years.

*Plant habit.*—Compact, mounding garden rose.

*Container size of plant described.*—3 gallon.

*Height.*—60 cm.

*Plant spread.*—65 cm.

*Rootstock.*—Un-grafted, plants grown on own roots.

*Growth rate.*—Moderate.

*Branching arrangement.*—Abundant branching. Dense lateral branching.

*Lateral branches.*—Quantity: Average 33. Diameter: Approximately 5 mm. Length: Approximately 32 cm. Color: Near Green 143C, flushed Greyed-Red 182B. Internode Length: Average 3.5 cm. Angle: Upright growth, branches at acute angles. Strength: Strong. Texture: Glabrous, less than moderately thorny. Thorns: Approximately density/quantity of thorns: Average 1 per linear cm. Shape: Narrow, bent downward. Oblanceolate base, acuminate apex. Color of thorns: Immature: Near Greyed-Red 181A. Mature: Near Greyed-Red 181A. Diameter: Average 6 mm at base. Height: Average 7 mm.

Foliage:

*Leaf.*—Arrangement: Alternate. Quantity: Approximately 7 per main branch. Average Length: Approximately 9.6 cm. Average Width: Approximately 5.8 cm.

*Leaflet.*—Quantity: 5, occasionally 3. Average Length: Terminal Length: Approximately 4.8 cm. Lateral Length: Approximately 4.0 cm. Average Width: Terminal Width: Approximately 3.1 cm. Lateral Width: Approximately 2.6 cm. Shape of blade: Elliptic. Apex: Acute. Base: Obtuse. Margin: Serrate. Appearance of top surface: Glossy. Appearance of bottom surface: Glossy. Texture of top surface: Glabrous. Texture of bottom surface: Glabrous. Leaf internode length: Average 2.0 cm. Color: Young foliage upper side: Near Yellow-Green 146A. Young foliage under side: Near Yellow-Green 146B. Mature foliage upper side: Near Green NN137A. Mature foliage under side: Near Yellow-Green 146B. Venation: Type: Pinnate. Venation color upper side: Near RHS Yellow-Green 144B. Venation color under side: Near RHS Yellow-Green 144B. Petiole: Length: 3.2 cm. Width: 2 mm. Color: Upper surface near RHS Yellow-Green 144B, with significant anthocyanin Red 51B. Lower surface near 144B. Texture: Glabrous upper surface, lower surface with microthorns. Leaflet Petiole: Length: 1.0 mm. Width: 1.0 mm. Color: Upper surface near RHS Red 50B; lower surface near 148A. Texture: Microthorns. Stipule: Quantity: 2. Shape: Falcate. Apex: Acuminate. Base: Oblique. Margin: Ciliate. Length: 22 mm. Width: 1.1 mm. Texture: Glabrous, upper and lower surfaces. Color: Upper surface near Yellow-Green 144B flushed Red 51B. Lower surface near Yellow-Green N144C. Foliage durability to stress: Good.

Flower:

*Natural flowering season.*—Spring through summer.

*Arrangement.*—Single occuring bloom at terminal branch ends. Evenly rotate, double or triple whorl.

*Flower size.*—Diameter: Approximately 7.0 cm. Depth: Approximately 2.1 cm.

*Peduncle.*—Length: 3.0 cm. Diameter: 2.7 mm. Strength: Strong. Angle: Upright, approximately 10 to 80°. Texture: Prickly. Color: Near Green 143C flushed Greyed-Red 182B.

*Petals.*—Petal arrangement: Rotate, overlapping double whorl. Length: 3.2 cm. Width: 3.1 cm. Shape: Obovate. Margin: Entire. Apex: Obcordate. Base: Obtuse. Petal quantity: Average 14 to 15. Texture: Glabrous, silky, upper and lower surfaces.

*Color.*—Petals: When opening: Upper surface: Mixture of RHS Yellow 9A, Orange 28A and Orange-Red 33A. Lower surface: Near RHS Yellow 12A and Yellow-Orange 21B. Fully opened: Upper surface: Mixture of RHS Yellow 9C and Orange 24A. Lower surface: Mixture of Yellow 9C and Orange-Red 30A. Color Changes when aging: Upper surface: Mixture of Yellow 10B with Red 36B. Lower Surfaces: Mixture of Yellow 10B with Red 36B.

*Petaloids*.—Arrangement: Whorled. Quantity: 0 to 4. Length: 1.8. Width: 1.0 cm. Shape: Irregular, various ovate shapes. Margin: Entire. Texture: Glabrous, silky, upper and lower surfaces. Color: When opening, both surfaces: Mixture of RHS Yellow 9A, Orange 28A and Orange-Red 33A. Mature, both surfaces: Mixture of RHS Yellow 9C, and Orange-Red 30A.

*Bud*.—Shape: Ovate. Length: Approximately 2.2 cm. Diameter: Approximately 1.2 cm. Color: Near RHS Yellow-Green 144A.

*Sepals*.—Quantity: 5. Arrangement: Whorled. Length: 3.1 cm. Width: 0.9 cm. Shape: Acuminate. Apex: Acuminate. Base: Truncate. Margin: Irregularly dissected. Color: Immature: Interior Surface: Near RHS Yellow-Green 144A. Exterior Surface: Near RHS Yellow-Green 144A. Mature: Interior Surface: Near RHS Yellow-Green 144A. Exterior Surface: Near RHS Green 143B. Texture: Interior surface pubescent, exterior surface glabrous. Fragrance: Lightly sweet.

Reproductive organs:

*Stamens*.—Number: 134. Filament length: Approximately 1.2 cm. Filament color: Near RHS Orange-Red 33B.

*Anthers*.—Length: 2.8 mm. Shape: Oblong. Color: Near RHS Yellow 13A. Pollen: Color: Near RHS Yellow 13A. Quantity: Moderate.

*Pistil*.—Quantity: 111. Length: 5.3 mm. Style: Length: Approximately 4.3 mm. Color: Near RHS Yellow 9C and Orange-Red N34B. Stigma: Shape: Globular cluster. Color: Near RHS Yellow 6A.

*Receptacle*.—Height: 12 mm. Diameter: 9 mm. Shape: Obovate. Texture: Smooth. Color: Near RHS Green 144B.

Other characteristics:

*Seeds and fruits*.—Not observed to date.

*Disease/pest resistance*.—Above average disease resistance to black spot and powdery mildew, typically found on garden roses. Average tolerance for typical garden rose pests.

What is claimed is:

1. A new and distinct cultivar of Floribunda rose plant named 'CHEWGEWEST', typically used as a garden rose, as herein illustrated and described.

* * * * *